US006618624B2

(12) United States Patent
Elias (10) Patent No.: US 6,618,624 B2
(45) Date of Patent: Sep. 9, 2003

(54) PROGRESSIVE RADIAL CORRECTION HAND DEVICE

(76) Inventor: Rebecca Lynn Elias, P.O. Box 447, Pine Valley, CA (US) 91962

( * ) Notice: Subject to any disclaimer, the term of this patent is extended or adjusted under 35 U.S.C. 154(b) by 0 days.

(21) Appl. No.: 09/887,921

(22) Filed: Jun. 22, 2001

(65) Prior Publication Data
US 2002/0198475 A1 Dec. 26, 2002

(51) Int. Cl.$^7$ ................................................ A61N 1/18
(52) U.S. Cl. ........................... 607/48; 128/879; 602/21; 607/145; 623/24
(58) Field of Search ................. 128/878–880; 601/15, 21; 602/2, 20–22, 64; 607/2, 3, 48, 145, 149, 150, 152; 623/24, 25, 57–65

(56) References Cited

U.S. PATENT DOCUMENTS

| 4,928,712 A | * | 5/1990 | Mele ........................... 128/877 |
| 5,540,735 A | * | 7/1996 | Wingrove .................... 607/46 |
| 5,891,068 A | | 4/1999 | Kenney |
| 6,458,091 B1 | * | 10/2002 | Parker et al. ................. 602/21 |

OTHER PUBLICATIONS

Sammons Preston Catalog Ability One 1999 pp. 289 & 349.
Concepts ADL Catalog undated p. 126.
Hand Therapy Catalog, North Coast Medical 1998 pp. 29, 51 & 79.

* cited by examiner

Primary Examiner—Jeffrey R. Jastrzab
Assistant Examiner—Frances P. Oropeza
(74) Attorney, Agent, or Firm—Howard R. Lambert (57) ABSTRACT

A progressive radial correction hand device for correcting ulnar finger deviation in a rheumatoid arthritic hand is described. The device comprises four elongate, soft, flexible finger straps, each of which is least about an inch wide in finger-contacting regions. Distal end regions of the finger straps are attached together to form a finger strap assembly. Described is a flexible fabric hand pad having finger and palm supporting regions and having a padded, hand-contacting upper region. The pad has a thumb-receiving aperture and four generally parallel slits formed in the palm supporting region for receiving, from the under side of the pad, the four finger straps. With the wearer's hand resting on the pad a strap with hook and loop strips attaches the pad to the hand and after the four finger straps are pulled upwardly from the pad over corresponding ones of the ulnar deviated fingers to urge the fingers toward a normal finger position, proximal ends of the finger straps are adjustably attached to distal ends of the straps by hook and loop strips. A stiff pad supporting member may be included and an electric stimulation current of between about 0.1 and 1.0 milliamps may be applied to radial muscle regions of the fingers and thumb of the hand to which the device is attached to strengthen the radial muscles.

19 Claims, 6 Drawing Sheets

PROGRESSIVE RADIAL CORRECTION HAND DEVICE

BACKGROUND OF THE INVENTION

1. Field of the Invention

The present invention relates generally to the field of medical devices, more particularly to devices used in medical therapy, and still more particularly to therapy devices for treating rheumatoid arthritic hands.

2. Background Discussion

Rheumatoid arthritis (also known as inflammatory arthritis) is a chronic systemic disease, primarily of the joints, marked by inflammatory changes in the synovial membranes and articular structures and by atrophy and rarefaction of the bones.

The cause of rheumatoid arthritis is currently unknown; however, autoimmune mechanisms and viral infections have been postulated (e.g., Dorland's Illustrated Medical Dictionary, $26^{th}$ Edition, 1985).

The physiological effects of rheumatoid arthritis, which can affect juveniles as well as adults, can range from discomfort and inconvenience to extreme pain and crippling disability. As yet no cure for rheumatoid arthritis is known, but medications, such as non-steroidal anti-inflammatory drugs (including aspirin and other salicitates), steroids, gold compounds, chloroquine or hydroxy chloroquine, penicillamine, immunosuppressive drugs, as well as cortisone injections may be beneficial in reducing joint inflammation and alleviating pain. For advanced rheumatoid arthritis, surgical procedures, including synovectomy, total joint replacement or anthroplasty may be required.

Although rheumatoid arthritis can affect any joints in a body, those of an individual's hands are perhaps most commonly affected, and it is to the treatment of this condition that the present invention is directed.

Figure 1A:
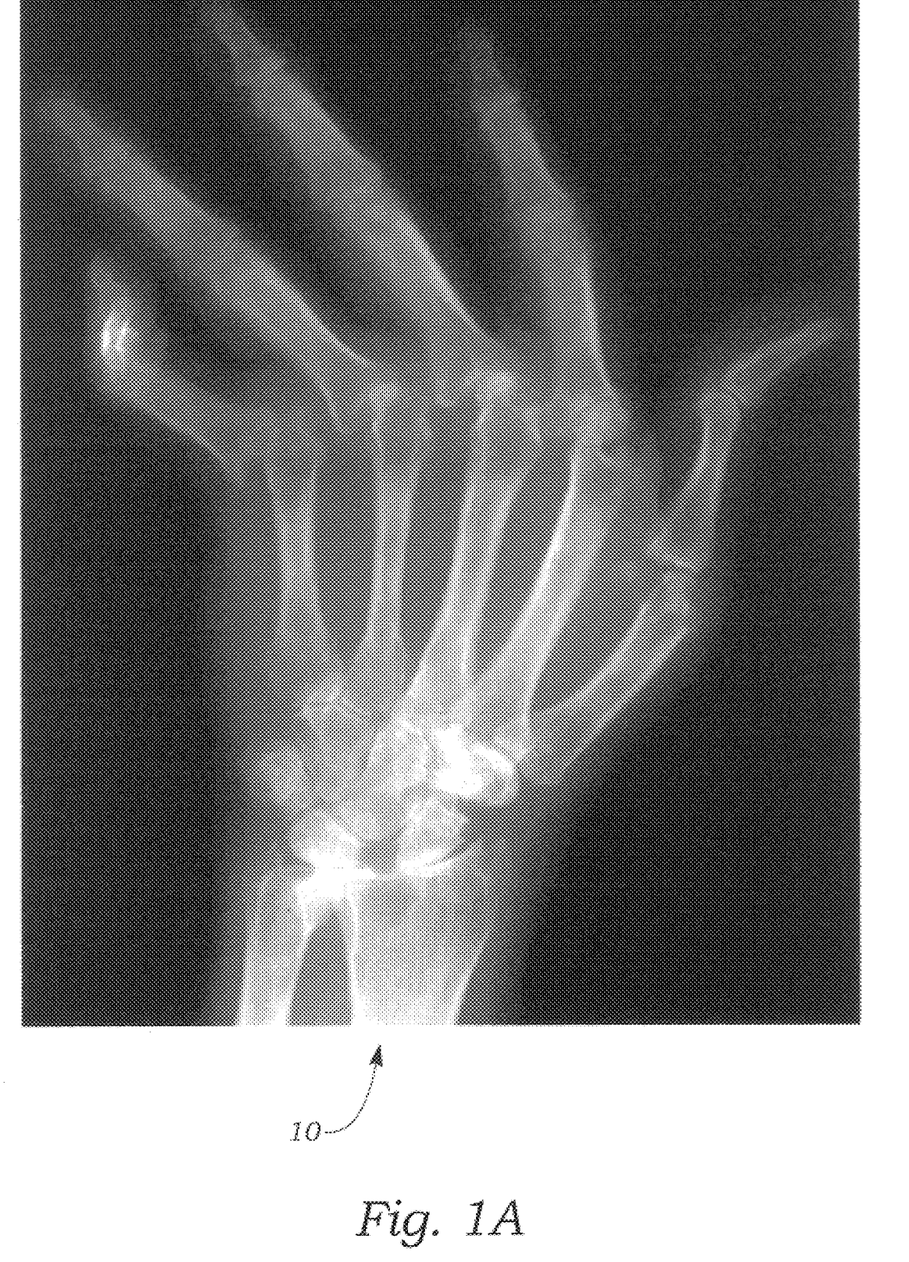
FIG. 1A is an X-ray photograph of a representative left hand afflicted by rheumatoid arthritis to the extent that severe ulnar finger deviation has resulted.

Shown, by way of example, in the X-ray photograph of FIG. 1A, attached hereto, is a representative hand that is severely afflicted by rheumatoid arthritis. The X-rayed hand is deformed at the metacarpalphalangeal joints (i.e., the knuckles) to an extent that the fingers are forced or pulled away from the thumb toward the little finger by the ulnar (as opposed to radial) muscles of the fingers. Such a depicted condition is frequently referred to as the ulnar deviation of the fingers, the word "ulnar" being derived from ulna, the inner and larger bone of the forearm on the side opposite to that of the thumb.

In addition to being usually extremely painful, severe ulnar deviation of the fingers by rheumatoid arthritis limits normal use of the hand, making, for example, the grasping and holding of objects and the performing of simple everyday tasks like eating and grooming, extremely painful and difficult or even impossible.

At this point it is important to distinguish the above-described condition of ulnar finger deviation caused by rheumatoid arthritis from the condition of ulnar deviation of an individual's hand. This latter term is ordinarily applied to movement of the wrist in the plane of the palm of the hand away from the thumb and toward the little finger and is typically associated with repetitive side-to-side motion of an individual's hand (relative to the forearm), for example, while using a typewriter or computer keyboard. This results in damage to the individual's ulnar nerve at the exit from the carpal tunnel near the elbow and the condition is generally called "carpal tunnel syndrome" (CTS).

As is well documented, CTS may, for example, be treated (or prevented) by the use of ergonomically-designed keyboards that require minimal hand movement during typing. Alternatively, or in addition, CTS may be treated or prevented by the application of rigid wrist braces or splints that lock the wrist in the neutral position, thereby relieving pressure in the carpel tunnel. Such braces or splints, which typically include straps around the base of the fingers, the wrist and forearm, prevent flexion, hyper-extension and ulnar deviation, and enable a wearer to keep working with reduced pain.

Ulnar finger deviation caused by rheumatoid arthritis is treatable in many cases. However, because of the different mechanisms involved, use of CTS wrist braces (splints) is not considered by the present inventor to be useful or even appropriate. For example, rheumatoid arthritis causes, as described above, ulnar deviation of the fingers, while CTS involved ulnar deviation of the entire hand. Moreover, the use of CTS devices for treating ulnar finger deviation caused by rheumatoid arthritis is contra-indicated due to risk of causing skin breakdown and pain. Still further, such CTS devices would not provide necessary finger muscle "reeducation" as is desired to restore ulnar finger deviation toward a normal condition.

Accordingly, a principal objective of the present invention is, therefore, to provide a hand-worn device for treating and/or correcting ulnar finger deviation caused by rheumatoid arthritis.

SUMMARY OF THE INVENTION

In accordance with the present invention, there is provided a progressive radial correction hand device for correcting ulnar finger deviation in a rheumatoid arthritic hand. The device comprises a flexible fabric hand pad having finger and palm supporting regions and having a soft, padded, non-skin irritating hand-contacting upper region and first, second, third and fourth elongate, flexible finger straps, each of the straps having a soft, non-skin irritating finger-contacting surface and being at least about an inch wide in finger-contacting regions, each of said finger straps having proximal and distal end regions. Preferably the pad is formed having a thumb-receiving aperture.

Included in the device are means for anchoring distal end regions of the finger straps at the palm supporting region of the pad, means for detachably attaching the hand supporting region of the pad to a wearer's hand, and means for adjustably and detachably attaching proximal ends of the four finger straps together at the distal end regions thereof with the wearer's hand resting on the pad and with the finger straps pulled upwardly from the pad upper region and over corresponding ones of the wearer's ulnar deviated fingers to urge the fingers toward a normal finger position.

Preferably, the distal end regions of all the finger straps are attached together to form a finger strap assembly and four generally parallel, spaced-apart slits are formed in a palm supporting region of the pad, each one of the slits being sized for receiving therethrough a corresponding one of the four finger straps from an under side of the pad.

There may be included a rigid pad supporting member positioned at an under surface of the pad, the supporting member being formed having four, generally parallel, spaced-apart slots corresponding to the four slits formed in the pad, so the finger straps can be received through the four slots in the pad supporting member before being received through the four slits in the pad.

It is also preferred that the device include means connected for applying an electric stimulation current to radial muscle regions of each of the four fingers, and preferably also to radial muscle regions of the thumb, of the hand to which the device is attached. The electric stimulation current provided is preferably between about 0.1 and about 1.0 milliamps.

More particularly, the progressive radial correction hand device for correcting ulnar finger deviation in a rheumatoid arthritic hand comprises first, second, third and fourth elongate, flexible finger straps, each of which has a soft, non-skin irritating finger-contacting surface and each having proximal and distal ends, the distal ends of all the finger straps being attached together to form a finger strap assembly.

Included is a flexible fabric hand pad having finger and palm supporting regions, having a soft, padded, non-skin irritating hand-contacting upper region and having a thumb-receiving aperture. The palm supporting region has four spaced-apart, generally parallel slits, each one of the slits being sized for receiving therethrough a corresponding one of the four finger straps from an under side of the pad. Further included are means for detachably securing the hand supporting region of the pad to a wearer's hand. Means are provided for adjustably and detachably attaching proximal ends of the four finger straps together at the distal ends thereof with the wearer's hand resting on the pad with the wearer's thumb extending through the thumb-receiving aperture and with the finger straps extending through the palm region slits and pulled up and over corresponding ones of the four fingers of the hand to which the device is attached to urge the wearer's fingers toward a normal finger position.

Preferably finger-contacting regions of each of the finger straps have a width of at least about one inch. Also preferably, the device includes a rigid pad supporting member having upper and lower surfaces and having four generally parallel slots formed therein for receiving corresponding ones of the four finger straps from the lower surface prior to the finger straps being inserted through the four hand pad slits.

The pad palm region is preferably formed having at least five spaced apart finger strap-receiving slits for enabling the selective inserting of the finger straps therethrough to thereby enable selective urging of the ulnar deviated fingers toward their normal finger position. Included are means connected for applying an electric stimulation current to radial muscle regions of each of the four fingers and thumb of the hand to which the device is attached.

Also more specifically, a progressive radial correction hand device for correcting ulnar finger deviation in a rheumatoid arthritic hand comprises a flexible fabric hand pad having finger and palm supporting regions and having a soft, padded, non-skin irritating hand-contacting upper region, the pad being formed having a thumb-receiving aperture; and first, second, third and fourth elongate, flexible finger straps having proximal and distal end regions, each of the straps having a soft, non-skin irritating finger-contacting surface and being at least about an inch wide in finger-contacting regions, each of said finger straps.

Means are included for anchoring distal end regions of the finger straps at the palm supporting region of the pad, as is a strap for detachably attaching the hand supporting region of the pad to a wearer's hand. Means are provided for adjustably and detachably attaching proximal ends of the four finger straps together at the distal end regions thereof with the wearer's hand resting on the pad and with the finger straps pulled upwardly from the pad upper region and over corresponding ones of the wearer's ulnar deviated fingers to urge said fingers toward a normal finger position. Preferably means are provided for applying an electric stimulation current between about 0.1 and about 1.0 milliamps to radial muscle regions of each of the four fingers and the thumb of the hand to which the device is attached.

Distal end regions of all the finger straps are attached together to form a finger strap assembly, and wherein the anchoring means includes four generally parallel, spaced-apart slits formed in the palm supporting region of the pad, each one of the slits being sized for receiving therethrough a corresponding one of the four finger straps from an under side of the pad. A rigid pad supporting member positioned at an under surface of the pad has four, generally parallel, spaced-apart slots corresponding to the four slits formed in the pad, the finger straps being received through the four slots in the pad supporting member before being received through the four slits in the pad

BRIEF DESCRIPTION OF THE DRAWINGS

The present invention can be more readily understood by a consideration of the following detailed description when taken in conjunction with the accompanying drawings, in which:

FIG. 6 is a series of three drawings showing individual component parts of the disassembled progressive radial correction hand device.

In the various FIGS. the same elements and features are given the same reference numbers.

DESCRIPTION OF THE PREFERRED EMBODIMENT

There is shown in FIG. 1A, by way of illustrative example, a plan-view X-ray photograph of a representative adult human left hand 10 that is afflicted by rheumatoid arthritis to the extent that the four fingers are severely angled from their neutral position toward the left (in the hand orientation depicted) at the metacarpalphalangeal (MP) joints, that is, the knuckle joints between the proximal phalanx of the fingers and the metacarpal bones of the hand. The purpose of including the X-ray photograph is to illustrate and emphasize the extent of ulnar finger deviation of human hands that is caused by rheumatoid arthritis.

Figure 1B:
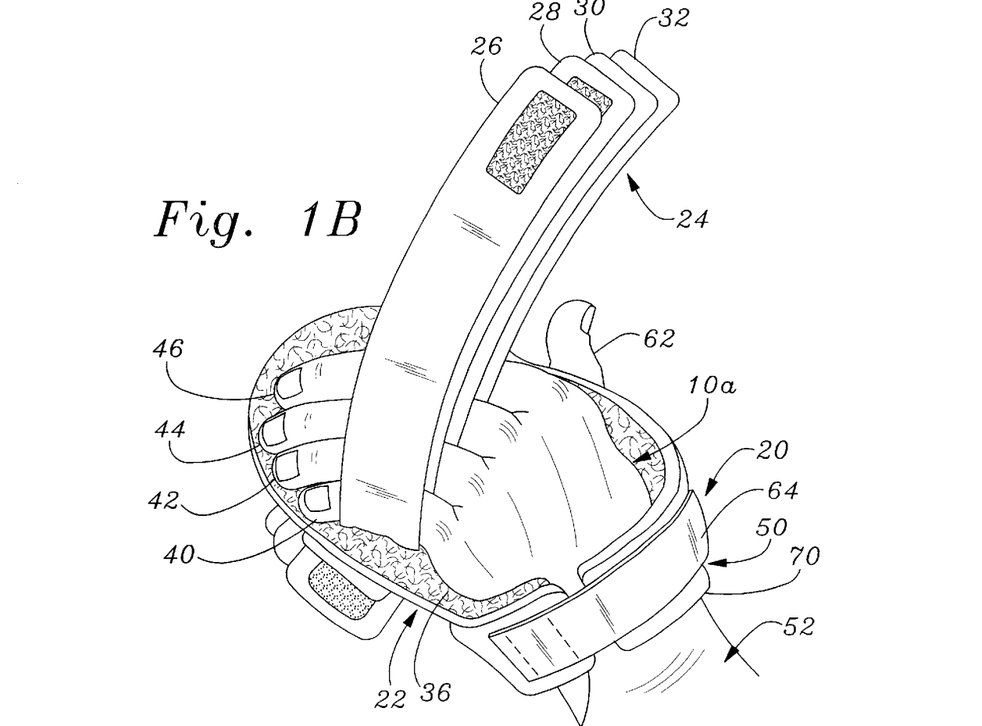
FIG. 1B is a perspective drawing showing the progressive radial correction hand device of the present invention in the process of being applied to an individual's left hand which exhibits severe ulnar deviation of the fingers such as is depicted in FIG. 1A.

FIG. 1B shows a static device 20, according to a preferred embodiment of the present invention, for treating ulnar finger deviation of the type depicted in the X-ray photograph of FIG. 1A. Device 20, termed by the present inventor as a radial correction hand device inasmuch as it supports weak radial muscles in the fingers, is shown supporting a hand 10a that generally corresponds to rheumatoid arthritis-deformed left hand 10 of FIG. 1A, and is principally intended for use at rest for pain reduction.

Shown in FIG. 1B comprising radial correction hand device 20, as more particularly described below, are a cushioned hand (that is, palm and finger) supporting pad 22 and a finger strap assembly 24 that includes respective first, second, third and fourth flexible fabric finger straps, 26, 28, 30 and 32. Electric muscle stimulation means, described below in connection with FIG. 7, may also be included.

As depicted, finger straps 26, 28, 30 and 32 are sized to extend from a soft upper layer 36 of hand supporting pad 22 up and over associated fourth (little) finger 40, third (ring) finger 42, second finger 44 and first (index) finger 46 (for the purposes of the following description, the thumb is not counted as the first finger as is done in some medical books) and are anchored to pad 22 as described below.

Included in device 20 are attaching means 50 fixed to hand supporting pad 24 for detachably and adjustably attaching the device to the wearer's hand adjacent the carpus (designated by reference number 52).

Figure 1C:
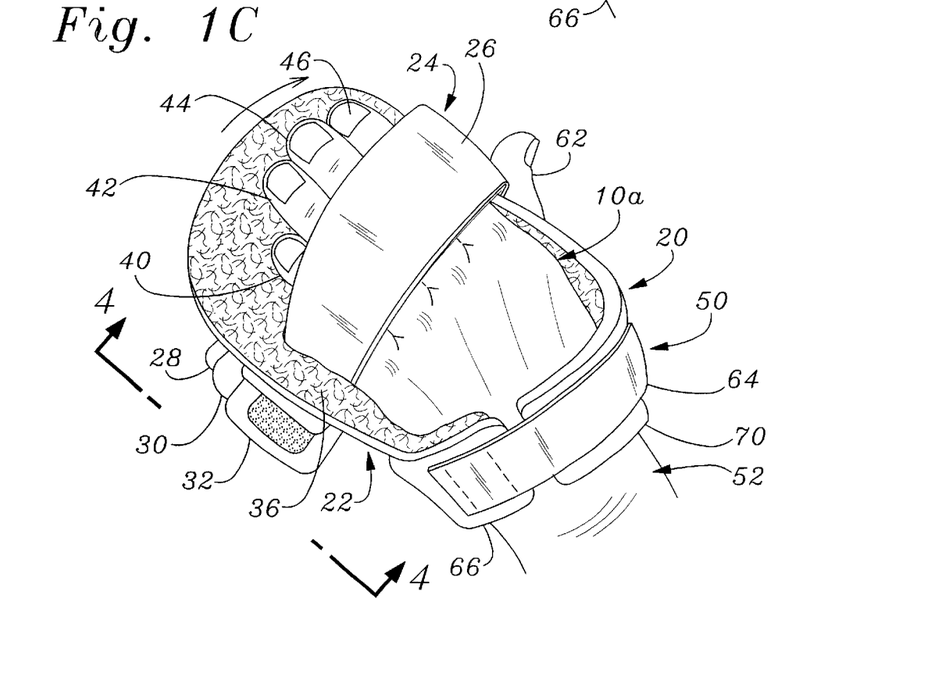
FIG. 1C is a perspective drawing showing the progressive radial correction hand device applied to the individual's left hand in a manner pulling the ulnar deviated fingers back to the neutral (straight-ahead) position.

FIG. 1C depicts radial correction hand device 20 fully applied to hand 10a so that finger straps 26–32, (only finger strap 26 actually being shown) pull ulnar deviated associated fingers 40–46 back toward or to their neutral position. Finger straps 26–32 are then secured by mating strips of hook and loop material as more particularly described below It should be understood that although FIG. 1C depicts device 20 applied to hand 10a in a manner completely pulling ulnar deviated fingers 40–46 back to their neutral position and retaining the fingers in the neutral position, finger straps 26–32 may be tightened in incremental steps so that the fingers are gradually pulled back (for example, over a period of time) to their neutral position through intermediate positions as may be needed or desired by the severity of ulnar finger deviation of hand 10a.

Figure 2:
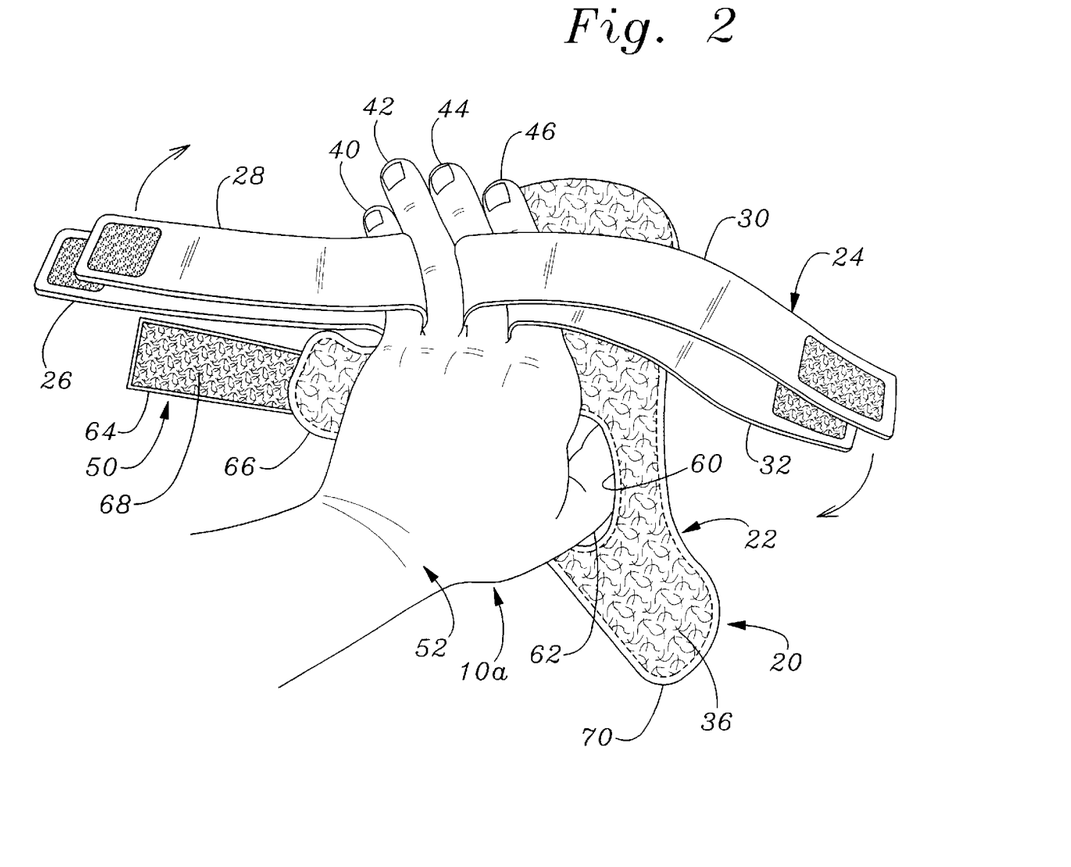
FIG. 2 is a perspective drawing of the progressive radial correction hand device of FIGS. 1A and 1B, showing the individual's left hand resting on a cushioned palm and finger pad of the device with the thumb inserted through a thumb-hole in the pad, and showing four flexible-fabric finger strap of the device positioned to engage all four ulnar deviated fingers of the individual's hand.

FIG. 2 depicts radial correction hand device 20 in the process of being applied to hand 10a and represents a step prior to that depicted in FIG. 1B. Shown formed in hand supporting pad 32 is an aperture 60 through which wearer's thumb 62 is inserted to maintain device 20 properly applied to hand 10a. First finger strap 26 is shown adjacent little finger 40, second finger strap 28 is shown extending between the little finger and ring finger 42, third finger strap 30 is shown extending between the ring finger and second finger 44, and fourth finger strap 32 is shown extending between the second finger and forefinger 46. Shown in FIG. 2 comprising attaching means 50 is an attaching strap 64 that is joined to a sidewardly extending region 66 of pad 22. Conventional hook and loop material strips (loop strip 68 attached to strap 64 being shown) are used to detachably attach strap 64 to an opposite, sidewardly extending region 70 of hand supporting pad 22.

Figure 3:
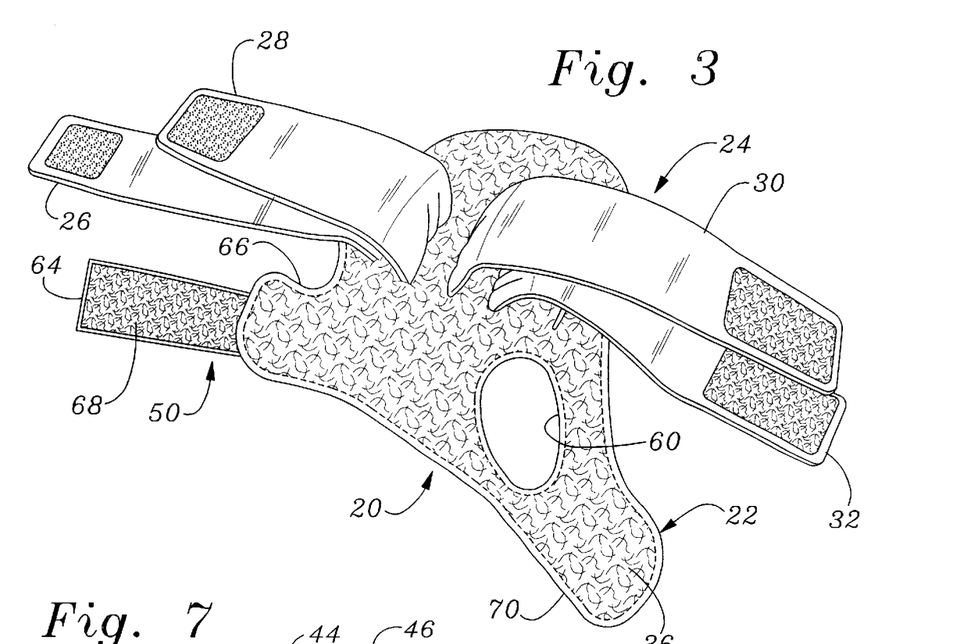
FIG. 3 is a perspective drawing of the correcting hand splint, similar to FIG. 3 except that the progressive radial correction hand device is shown not applied to a hand, showing the cushioned palm and finger pad and four flexible finger straps connected to the pad.

FIG. 3 is similar to FIG. 2 described above, except that device 20 is not shown supporting hand 10a in order to more clearly show the device as it is laid out ready to be applied to a hand.

Figure 4:
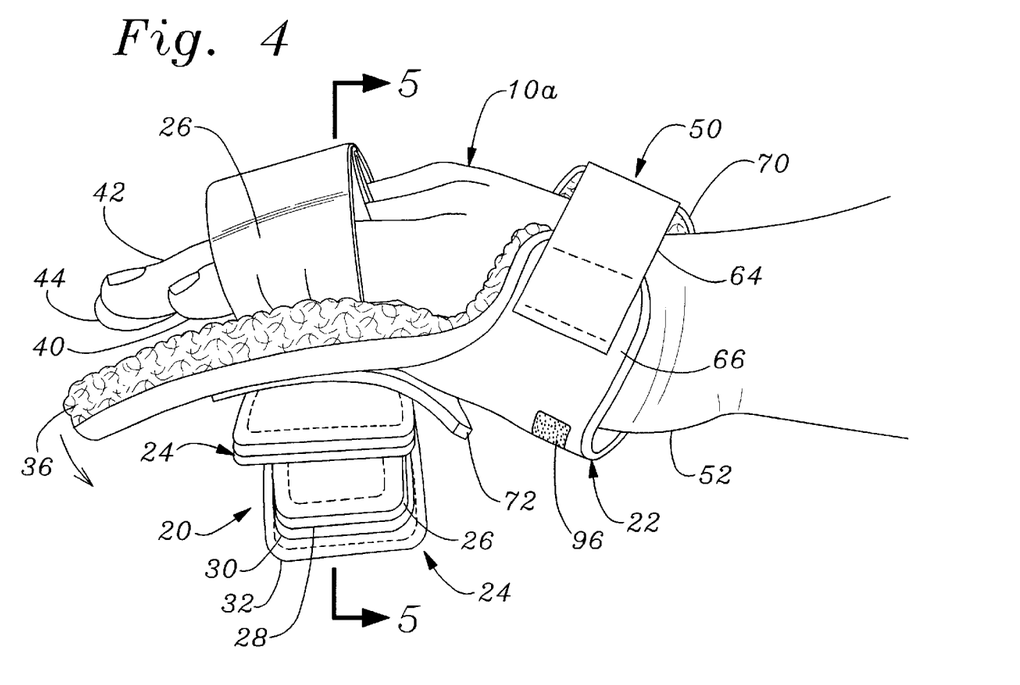
FIG. 4 is a view taken along line 4—4 of FIG. 1B, showing a side view of the progressive radial correction hand device applied to the individual's left hand, showing the cushioned palm and finger pad and showing a rigid, curved pad support member through which the finger straps extend before extending through the pad and up and over the individual's ulnar deflected fingers.

FIG. 4, is a side view of radial correction hand device 20 attached to hand 10a, showing the hand positioned on upper layer 36 of hand supporting pad 22, with the pad detachably attached to the hand by strap 64, and with finger straps passing up and fingers of the hand, (only finger strap 26 and fingers 40, 42 and 44 being shown). Further shown is a rigid, curved member 72 (described below) that is provided beneath pad 22 to stiffen the pad and keep the fingers of hand 10a resting on upper layer 36 of the pad from curling, as may frequently be desired.

Figure 5:
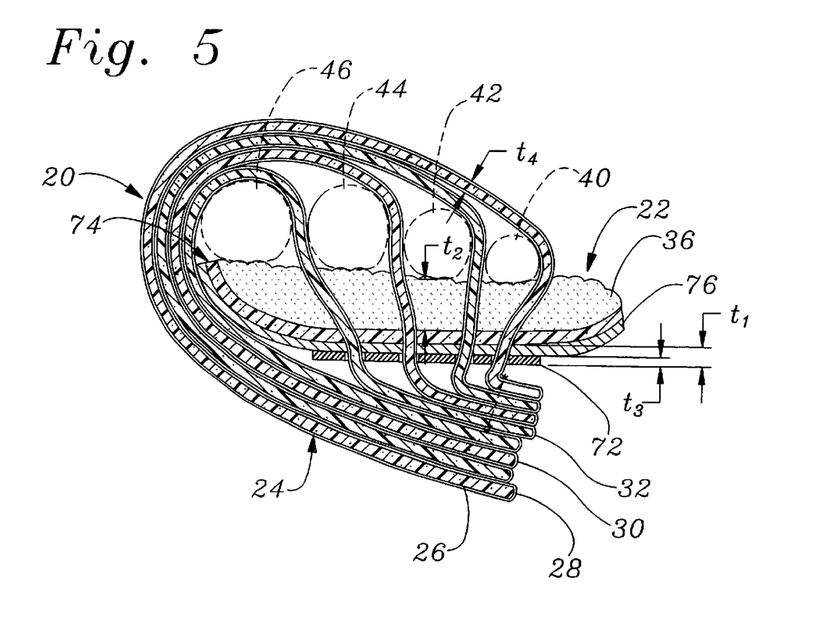
FIG. 5 is a cross sectional view taken along line 5—5 of FIG. 4, showing the arrangement of the cushioned palm and finger pad, support member and the four flexible finger straps passing up and over the individual's four fingers of the left hand.
Figures 6A, 6B, 6C:
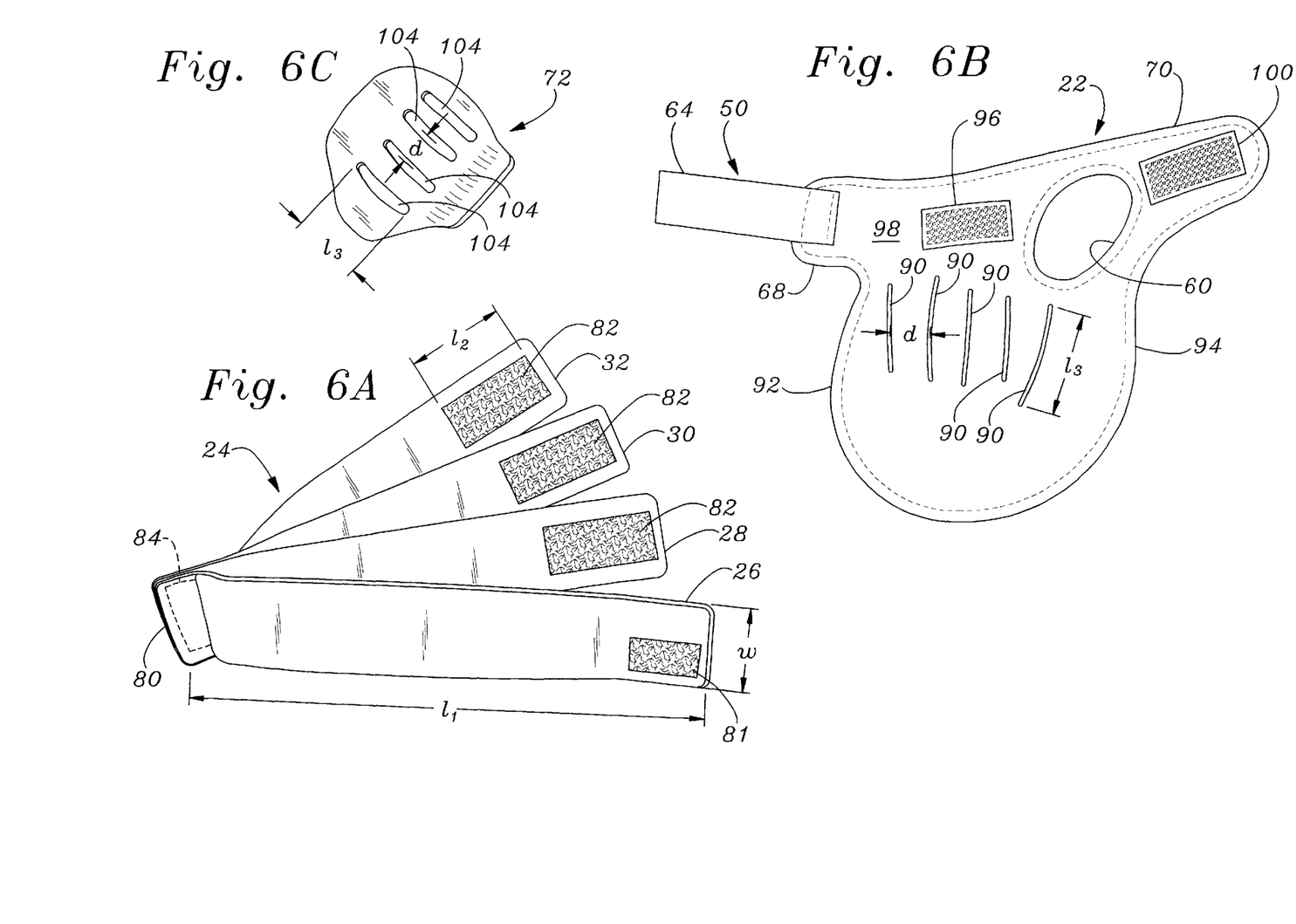
FIG. 6A being a plan view of the four flexible finger straps showing their overlaying arrangement.
FIG. 6B being a plan view of the cushioned palm and finger pad, showing five slits through which the four finger straps are selectively installed.
FIG. 6C being a plan view of the pad support member, showing four slits through which the four finger straps are installed.

Finger straps 26, 28, 30 and 32 of finger strap assembly 24, are shown in FIG. 5 extending up (for the orientation depicted) through corresponding narrow slots in both curved member 72 and hand pad 22 (see FIGS. 6B and 6C for slot details). As depicted, finger straps 26–32 overlay one another as they pass over fingers 40–46 and over and around a side edge 74 of pad 22. Proximal ends of finger straps 26–32 detachably and adjustably attach to one another as by hook and loop strips and to distal ends of the straps to secure the straps in place and to retain fingers 40—40 in the desired position.

As shown in FIG. 5, hand-supporting pad 22 includes a lower layer 76 having a thickness, $t_1$, that may be about 1/16 inch and may be constructed of a pliable but relatively stiff fabric. Upper layer 38 of pad 22 has a thickness, $t_2$, that is preferably between about 3/16 inch and about 3/8 inch. Curved member 72 preferably has a thickness, $t_3$, that is between about 1/16 and about 1/8 and is preferably constructed of a shape-retaining plastic that can be shaped after heating. Finger straps 26–32, all of which are preferably identical preferably have a thickness, $t_4$, (shown in FIG. 5 only for representative for strap 26) of about 1/8 inch.

With respect to construction of pad 22 and finger straps 26–32, it is important to understand that a hand deformed by rheumatoid arthritis will generally, if not always, be extremely sensitive to pain and irritation and may be subject to skin breakdown. Therefore pad 22 and finger straps 26–32 are necessarily constructed to be gentle while at the same time enabling correction of fingers 40–46. Desirably, device 20 is constructed so that it can be washed as may be needed.

To this end, pad upper layer 36 is preferably constructed of a soft, non-skin irritating, cushioning material, such as wool or polyester fleece. Upper and lower layers 38 and 74 of pad 22 are preferably sewn together, at least around their edges and around thumb aperture 60 (see FIG. 6B) so the pad retains its shape. In turn, finger straps 26–32 are preferably constructed from a smooth, soft, non-skin irritating, material, such as polyester, with non-exposed stitching that could cause finger skin irritation. Also preferably, finger straps 26–32 are made slightly stretchable, as by including a small percentage of LYCRA material, so that on pulling against associated fingers 40–46, the straps will conform to the shape of the fingers without creating painful pressure points.

FIG. 6 shows additional details of device 20, finger strap assembly 24 being shown in FIG. 6A, the under side of hand pad 22 being shown in FIG. 6B and support member 72 being shown in FIG. 6C.

Preferably, as shown in FIG. 6A, all finger straps 26, 28, 30 and 32 are constructed the same, each having a preferred width, w, (shown for strap 26) of between about 1 inch and about 1½ inches, end each having a preferred straight-line length, $l_1$, of at least about 8 inches (also shown for strap 26). All four finger straps 26–32 are fastened together at one end (identified by reference number 80) as by sewing individual strap ends together in an overlaying arrangement. Mating strips of hook and loop material, having lengths, 12, of about 1 to about 2 inches, are sewn to the free end regions of each of finger straps 26–32.

As shown, a loop material strip 81 is attached to one side of the free end region of finger strap 26 and wider loop material strips 82 are similarly attached to one side of the free end region of finger straps 28, 30 and 32. Mating hook material strips (not shown) are attached to the side of finger straps 26–32 opposite loop strips 81, 82 so that the free ends of the finger straps can be adjustably and detachably attached to one another when device 20 is applied to hand 10a, an additional mating hook material strip 84 (shown in broken lines) is attached to finger strap end 80 to enable fourth finger strap 32 to be adjustably and detachably attached to such end 80 when device 20 is applied to hand 10a as shown in FIG. 5.

Particularly shown in FIG. 6B are five elongate, spaced apart finger strap receiving slits or slots 90 that are formed through hand pad 22 in a long direction generally parallel to one another and to opposing side edges 92 and 94 of the pad. Moreover, slits 90 are positioned in pad 22 so that finger straps 26–32 extending through the slits will be positioned over the middle phalanx of each finger 40–46 (FIGS. 1A, 1B, 2 and 4) of hand 10a supported by the pad. Although four such slits 90 are provided for receiving separate ones of finger straps 26–32, at least a fifth such slit is preferably provided to enhance finger strap positional adjustment according to the size and condition of hand 10a.

Each of slits 90 preferably have a length, $l_3$, that is slightly longer than above-described finger strap width, w, the slits being spaced apart a common distance, d, that is preferably about a corresponding width of fingers 40–46 of hand 10a. Hand pad 22 is sized to fully support hand 10a, including fingers 40–46, and preferably to extend a short distance to the sides of hand, particularly, the thumb side of the hand, and beyond the distal ends of fingers 40–46.

A hook material strip 96 is attached to hand pad under surface 98. As indicated in FIG. 4, the free end region of pad 22 may, with pad support 72 deleted, be bent down in the direction of the arrow, thereby twisting over finger straps 26–32 until loop material strip 81 (not shown) on finger strap 26 engages hook material strip 96 on pad 22. Such configuration of pad 22 provides support for fingers 40–46 if they are in a curled condition, as may be caused by rheumatoid arthritis.

Another hook material strip 100 is attached to hand pad under surface 98 in hand pad region 70 for detachable engagement by loop material strip 68 on strap 64 (FIG. 3).

As shown in FIG. 6C, support member 72 is formed having four spaced apart finger strap receiving slots 108 having lengths, $l_3$, as above described. Although a fifth slot (similar to slots 104) may be provided, the present inventor considers that a fifth slot is unnecessary since support member 72 is not attached to hand pad 22 other than by finger straps 26–32 passing upwardly through support member slots 104 and hand pad slits 90. Thus, although slots 104 are generally spaced apart the same distance, d, as pad slits 90, the support member 72 is relatively free to be shifted at least slightly with respect to pad 22 (see FIG. 5). Support member 72 is sized to fit under a finger-supporting region of hand pad 22 and is intended for use for mild to moderate rheumatoid arthritis.

It will, of course, be appreciated that hand pad 22 and finger straps 26–32 are sized as required to fit hands of different sizes, the pad being sufficiently large to support the entire hand (corresponding to hand 10a) including the fingers (corresponding to fingers 40–46). Moreover, although device 20 has been shown and described above as a left-hand device for treating rheumatoid arthritis of an individual's left hand 10a, it will be understood that a right-hand device will simply be a mirror image of the left-hand device.

Device 20 can, as described above, be used to advantage to urge ulnar deviated fingers, for example, fingers 40–46 of hand 10a suffering from rheumatoid arthritis, to or toward their neutral positions and thereby provide comfort to the afflicted hand.

The present inventor has further discovered that important additional benefits in the treatment of hand 10a crippled by rheumatoid arthritis can be achieved by the incorporation of electric muscular stimulation (EMS) means 110 (FIG. 7) in progressive radial correction device 20. Pad 22 and finger strap assembly 24 are shown in phantom lines in FIG. 7 for purposes of clarity.

Figure 7:
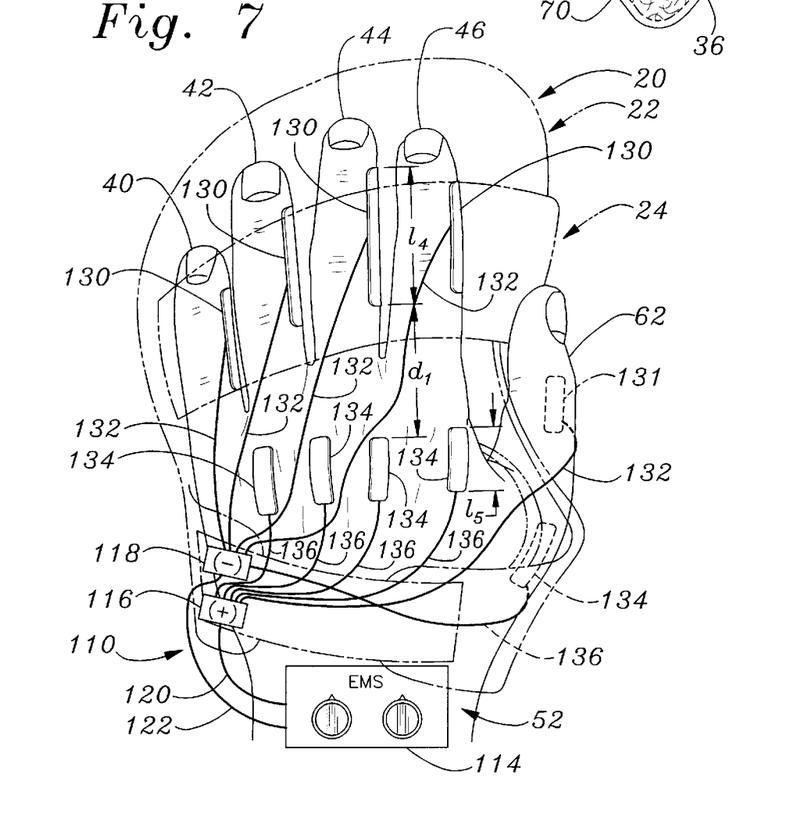
FIG. 7 is a plan view of the individual's left hand showing in phantom lines the radial correcting hand device applied to the hand and showing in solid lines an associated set of positive and negative electrodes attached to the fingers and thumb of the hand to provide electrical stimulation to the fingers and thumb for radial muscle strengthening.

As more particularly described below, EMS means 110, by applying a small electric current to radial muscle regions of fingers 40–46 (on thumb sides of the fingers opposite to the ulnar muscles), strengthens and "reeducates" the radial finger muscles when device 24 has returned fingers 40–46 to or toward their neutral position so the radial finger muscles can overcome the force of the ulnar finger muscles that cause ulnar finger deviation. Moreover, thumb 62 of hand 10a is also usually affected and weakened by rheumatoid arthritis, making the firm gripping and holding of objects between the thumb and fingers 40–46 difficult or impossible. Therefore, EMS means 110 is preferably (but not necessarily) also configured for applying a small electric current to radial muscle regions of thumb 62.

Shown in FIG. 7 comprising EMS means 110 are an EMS voltage supply and control unit 114, a positive (+) voltage terminal strip 116 and a negative (−) voltage terminal strip 118. Positive voltage terminal strip 116 is connected to supply and control unit 114 by an electrical conduit 120 and negative voltage terminal strip 118 is connected to the supply and control unit by an electrical conduit 122.

Five negative electrodes 130, which are preferably of the flexible, self-adhesive type and preferably have a length, $l_4$, of about 1½ inches—except for negative electrode 131 on thumb that is only about 1 inch long—and have a width that is between about ¼ inch to about ½ inch, are removably attached to radial muscle, side regions of fingers 40, 42, 44 and 46 and of thumb 62, avoiding finger and thumb MP joint regions as much as practical. Negative electrodes 130 are individually connected to negative voltage terminal strip 118 by electrical conduits 132.

Five positive electrodes 134, which are similar to negative electrodes 130, except for having a preferred length, $l_5$ of about 1 inch, are attached to dorsal interossei muscle regions of hand 10*a* a distance, $d_1$, of about 2 inches toward carpus 52 from corresponding ones of negative electrodes 130 and 131. Positive electrodes 134 are individually connected to positive voltage terminal strip 116 by electrical conduits 136.

Terminal strips 116 and 118 and electrical conduits 132 and 136 are preferably detachably attached, for example, by strips of mating hook and loop material to device hand strap 64.

EMS voltage supply and control unit 114 is preferably powered by a conventional 9 volt dry cell battery and is constructed in a known manner for providing an output current between pairs of negative and positive electrodes 130, 131 and 134 preferably of between about 0.1 and about 1.0 milliamps, with a duty cycle that is preferably variable between about 10% and about 100%. Unit 114 is preferably made as small as possible, for example, no larger than about the size of a deck of playing cards, and may, for example, be conveniently be clipped to hand strap 64 strap by a clip (not shown) attached to the back of the unit.

Although there has been described above a progressive radial correction hand device, in accordance with the present invention for purposes of illustrating the manner in which the present invention may be used to advantage, it is to be understood that the invention is not limited thereto. Consequently, any and all variations and equivalent arrangements that may occur to those skilled in the applicable art are to be considered to be within the scope and spirit of the invention as set forth in the claims, which are appended hereto as part of this application.

What is claimed is:

1. A progressive radial correction hand device for correcting ulnar finger deviation in a rheumatoid arthritic hand, said device comprising:
   a. a flexible fabric hand pad having finger and palm supporting regions and having a soft, padded, non-skin irritating hand-contacting upper region;
   b. first, second, third and fourth elongate, flexible finger straps, each of said straps having a soft, non-skin irritating finger-contacting surface and being at least about an inch wide in finger-contacting regions, each of said finger straps having proximal and distal end regions;
   c. means for anchoring distal end regions of said finger straps at the palm supporting region of said pad;
   d. means for detachably attaching the hand supporting region of the pad to a wearer's hand; and
   e. means for adjustably and detachably attaching proximal ends of said four finger straps together at the distal end regions thereof with the wearer's hand resting on the pad and with the finger straps pulled upwardly from the pad upper region and over corresponding ones of the wearer's ulnar deviated fingers to urge said fingers toward a normal finger position.

2. The progressive radial correction hand device as claimed in claim 1, wherein the distal end regions of all said finger straps are attached together to form a finger strap assembly.

3. The progressive radial correction hand device as claimed in claim 2, wherein said anchoring means includes four generally parallel, spaced-apart slits formed in a palm supporting region of said pad, each one of said slits being sized for receiving therethrough a corresponding one of said four finger straps from an under side of the pad.

4. The progressive radial correction hand device as claimed in claim 3, including a rigid pad supporting member positioned at an under surface of said pad, said supporting member being formed having four, generally parallel, spaced-apart slots corresponding to the four slits formed in said pad, said finger straps being received through the four slots in the pad supporting member before being received through the four slits in the pad.

5. The progressive radial correction hand device as claimed in claim 1, wherein said pad is formed having a thumb-receiving aperture.

6. The progressive radial correction hand device as claimed in claim 1, including means connected for applying an electric stimulation current to radial muscle regions of each of the four fingers of said hand to which the device is attached.

7. The progressive radial correction hand device as claimed in claim 6, wherein said electric stimulation means is connected for applying an electric stimulation current to radial muscle regions of the thumb of said hand to which the device is attached.

8. The progressive radial correction hand device as claimed in claim 6, wherein said electric stimulation current is between about 0.1 and about 1.0 milliamps.

9. A progressive radial correction hand device for correcting ulnar finger deviation in a rheumatoid arthritic hand, said device comprising:
   a. first, second, third and fourth elongate, flexible finger straps, each of said straps having a soft, non-skin irritating finger-contacting surface and each having proximal and distal ends, the distal ends of all said straps being attached together to form a finger strap assembly;
   b. a flexible fabric hand pad having finger and palm supporting regions, having a soft, padded, non-skin irritating hand-contacting upper region and having a thumb-receiving aperture, said palm supporting region having four spaced-apart, generally parallel slits, each one of said slits being sized for receiving therethrough a corresponding one of said four finger straps from an under side of the pad;
   c. means for detachably securing the hand supporting region of the pad to a wearer's hand; and
   d. means for adjustably and detachably attaching proximal ends of said four finger straps together at the distal ends thereof with the wearer's hand resting on the pad with the wearer's thumb extending through the thumb-receiving aperture and with the finger straps extending through the palm region slits and pulled up and over corresponding ones of the four fingers of the hand to which the device is attached to urge the wearer's fingers toward a normal finger position.

10. The progressive radial correction hand device as claimed in claim 9, wherein finger-contacting regions of each of the finger straps has a width of at least about one inch.

11. The progressive radial correction hand device as claimed in claim 9, including a rigid pad supporting member having upper and lower surfaces and having four generally parallel slots formed therein for receiving corresponding ones of the four finger straps from said lower surface prior to the finger straps being inserted through the four hand pad slits.

12. The progressive radial correction hand device as claimed in claim 9, wherein said pad palm region is formed having at least five spaced apart finger strap-receiving slits for enabling the selective inserting of the finger straps therethrough to thereby enable selective urging of said fingers toward said normal finger position.

13. The progressive radial correction hand device as claimed in claim 9, including means connected for applying an electric stimulation current to radial muscle regions of each of the four fingers of said hand to which the device is attached.

14. The progressive radial correction hand device as claimed in claim 13, wherein said electric stimulation means is connected for applying an electric stimulation current to radial muscle regions of the thumb of said hand to which the device is attached.

15. A progressive radial correction hand device for correcting ulnar finger deviation in a rheumatoid arthritic hand, said device comprising:
   a. a flexible fabric hand pad having finger and palm supporting regions and having a soft, padded, non-skin irritating hand-contacting upper region, said pad being formed having a thumb-receiving aperture;
   b. first, second, third and fourth elongate, flexible finger straps, each of said straps having a soft, non-skin irritating finger-contacting surface and being at least about an inch wide in finger-contacting regions, each of said finger straps having proximal and distal end regions;
   c. means for anchoring distal end regions of said finger straps at the palm supporting region of said pad;
   d. a strap for detachably attaching the hand supporting region of the pad to a wearer's hand;
   e. means for adjustably and detachably attaching proximal ends of said four finger straps together at the distal end regions thereof with the wearer's hand resting on the pad and with the finger straps pulled upwardly from the pad upper region and over corresponding ones of the wearer's ulnar deviated fingers to urge said fingers toward a normal finger position; and
   f. means connected for applying an electric stimulation current to radial muscle regions of each of the four fingers of said hand to which the device is attached.

16. The progressive radial correction hand device as claimed in claim 15, wherein the distal end regions of all said straps are attached together to form a finger strap assembly, and wherein said anchoring means includes four generally parallel, spaced-apart slits formed in the palm supporting region of said pad, each one of said slits being sized for receiving therethrough a corresponding one of said four finger straps from an under side of the pad.

17. The progressive radial correction hand device as claimed in claim 16, including a rigid pad supporting member positioned at an under surface of said pad, said supporting member being formed having four, generally parallel, spaced-apart slots corresponding to the four slits formed in said pad, said finger straps being received through the four slots in the pad supporting member before being received through the four slits in the pad.

18. The progressive radial correction hand device as claimed in claim 15, wherein said electric stimulation means is connected for applying an electric stimulation current to radial muscle regions of the thumb of said hand to which the device is attached.

19. The progressive radial correction hand device as claimed in claim 15, wherein said electric stimulation current is between about 0.1 and about 1.0 milliamps.

* * * * *